(12) United States Patent
Roeder et al.

(10) Patent No.: US 9,216,301 B2
(45) Date of Patent: *Dec. 22, 2015

(54) BALLOON CATHETER AND APPLICATOR WITH BALLOON CATHETER (71) Applicant: Carl Zeiss Meditec AG, Jena (DE)

(72) Inventors: Norman Roeder, Aalen (DE); Matthias Benker, Heidenheim (DE)

(73) Assignee: CARL ZEISS MEDITEC AG, Jena (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/031,096

(22) Filed: Sep. 19, 2013

(65) Prior Publication Data

US 2014/0107472 A1    Apr. 17, 2014

Related U.S. Application Data (62) Division of application No. 12/592,769, filed on Dec. 2, 2009.

(30) Foreign Application Priority Data

Dec. 2, 2008   (DE) .......................... 10 2008 060 162

(51) Int. Cl.
*A61N 5/10*       (2006.01)
*A61M 25/10*    (2013.01)
*A61B 5/06*       (2006.01)

(52) U.S. Cl.
CPC .............. *A61N 5/1014* (2013.01); *A61B 5/061* (2013.01); *A61M 25/1011* (2013.01); *A61N 5/1015* (2013.01); *A61M 25/1002* (2013.01); *A61M 2025/1013* (2013.01)

(58) Field of Classification Search
CPC ... A61N 5/1014; A61N 5/1015; A61B 5/061; A61B 2017/22051; A61B 2017/22048; A61B 2017/22054; A61M 25/1011; A61M 25/1002; A61M 2025/1015; A61M 2025/1013
USPC .................... 600/3; 604/96.01, 97.01, 103.01
See application file for complete search history.

(56) References Cited

U.S. PATENT DOCUMENTS 5,447,497 A    9/1995   Sogard et al.
5,621,780 A    4/1997   Smith et al.

(Continued)

FOREIGN PATENT DOCUMENTS

DE    69314116 T2    3/1998
EP    0850660 B1    9/2003

(Continued)

*Primary Examiner* — Jacqueline Cheng
*Assistant Examiner* — Kaylee Wilson
(74) *Attorney, Agent, or Firm* — Kriegsman & Kriegsman (57) ABSTRACT

Balloon catheter, applicator, particularly for invasive radiotherapy, and method of controlling the balloon catheter with respect to its shape and position in a tissue to be treated prior to an irradiation. The balloon catheter provides a catheter shaft for introducing a probe, an outer balloon and an inner balloon, disposed inside the outer balloon, the inner space of the inner balloon connecting to a channel for connection to a media inlet and intermediate space between the outer balloon and the inner balloon connecting to a channel for connection to a media storage unit. In order that the balloon catheter can be securely controlled with respect to its shape and position in a patient in a simple but clear manner prior to irradiation, the outer balloon is formed of a flexible, non-extendible material and the inner balloon is formed of a flexible, extendible material.

5 Claims, 4 Drawing Sheets

(56) References Cited

U.S. PATENT DOCUMENTS

| | | | |
|---|---|---|---|
| 5,797,948 A | 8/1998 | Dunham | |
| 6,733,474 B2 * | 5/2004 | Kusleika | 604/103.01 |
| 6,923,754 B2 | 8/2005 | Lubock | |
| 2005/0080313 A1 | 4/2005 | Stewart et al. | |
| 2007/0191667 A1 * | 8/2007 | Lubock et al. | 600/3 |
| 2008/0004479 A1 * | 1/2008 | Stewart et al. | 600/3 |
| 2008/0140001 A1 | 6/2008 | Globerman et al. | |
| 2008/0177127 A1 | 7/2008 | Allan et al. | |

FOREIGN PATENT DOCUMENTS

| | | |
|---|---|---|
| GB | 2415907 A | 1/2006 |
| WO | 9904856 A1 | 2/1999 |
| WO | 2008077073 A2 | 6/2008 |

* cited by examiner

BALLOON CATHETER AND APPLICATOR WITH BALLOON CATHETER

BACKGROUND OF THE INVENTION

The present invention first relates to a balloon catheter, in particular for invasive radiotherapy, with a catheter shaft for introducing a probe, having a first, outer balloon and having a second, inner balloon, disposed inside the outer balloon, the inner space of the second, inner balloon connecting with a channel for connection to a media inlet, and intermediate space between the first, outer balloon and the second, inner balloon connecting to a channel for connection to a media storage unit. In addition, the invention also relates to an applicator, in particular for invasive radiotherapy, having a balloon catheter, with a catheter shaft for introducing a probe, having a first, outer balloon made of a flexible, non-extendible material and a second, inner balloon made of a flexible, extendible material disposed inside outer balloon, additionally having an inside space of the second, inner balloon, which is connected via a connection channel at least temporarily with a media inlet, and additionally having an intermediate space between the first, outer balloon and the second, inner balloon, which is connected via a connection channel at least temporarily with a media storage unit. Moreover, the invention further relates to a method of controlling a balloon catheter with respect to its shape and position in a tissue to be treated prior to an irradiation, wherein the balloon catheter is part of an applicator and also relates to a method of irradiating a tumor bed by use of a balloon catheter, wherein the balloon catheter is part of an applicator.

In invasive radiation therapy of tumors, there exist different methods for irradiating the tumor, or for irradiating the tumor bed after lumpectomy has been performed. For this, access to the tumor or to the remaining tumor bed must be created. This access, which is temporary, can be made possible by means of a balloon catheter, which can function as a type of place holder, especially in the case of irradiation of a tumor bed.

Most frequently, the balloon catheter, which is folded together, is put in place via a biopsy channel created therefor. The balloon is subsequently filled with a medium, so that it assumes its defined shape. Such a balloon catheter is disclosed, for example, in U.S. Pat. No. 5,621,780 A.

An isotonic saline solution is often used as a filling medium. This is used first and foremost in order to minimize the risk to the patient in the case of a balloon rupture due to pressurized filling medium, since water can hardly be compressed. In addition, a physiological saline solution can better assure the dimensional stability of the balloon than gases, for example.

In addition to access to the tumor bed, the balloon catheter has the task of providing a defined shape, preferably a spherical shape, to the tumor bed that is dimensionally unstable. Other geometries are also possible, however. A uniform irradiation of the surrounding tissue will thus be made possible without complex irradiation planning.

In this method, for irradiation planning, it is important to know whether the actual shape of the balloon is also the desired or necessary shape. The shape may deviate from the defined basic form due to particular local features, especially in balloons which are made of extendible material.

An increase in internal pressure due to the introduction of additional media does not offer a solution here, since the balloon would only be further extended, increasing the risk of a balloon rupture.

If a deviation in shape is not noticed, because of different distances, erroneous irradiation of the surrounding tissue will occur.

The application of "solid applicators" would be ideal here. The solid structure used would ideally suppress the surrounding tissue and thus make possible a molding of the tissue around the applicator. Solid applicators guarantee a stable arrangement during the irradiation. However, based on their primary property, they are not suitable for application in the case of fractionated irradiation, since they cannot be removed in a minimally invasive manner after the irradiation.

In order to assure the balloon shape, this shape is tested in practice with different imaging methods after the balloon is placed in the body. After the irradiation, which may extend over several irradiation sessions, the filling medium can be aspirated and the balloon catheter can be removed through the biopsy channel.

Techniques such as computed tomography (CT) or ultrasound are used very frequently for visualizing the balloon catheter in the patient. In this case, however, imaging is made difficult due to the special properties of the balloon catheter. Once the balloon is filled, usually with an aqueous solution, for shaping, the balloon can barely be distinguished from the surrounding tissue. This makes imaging by CT or ultrasound difficult. Air would be rather well suitable for visualizing. Based on its high compression, which is required for dimensional stability, however, this medium is associated with an elevated risk for the patient. Therefore, materials or structures that absorb x-rays and are found in or on the balloon walls must be used in CT in order to make the balloon catheter visible. There is also the possibility of filling the balloon with a contrast agent or a water/contrast agent mixture.

In addition to the radiation load due to CT that is based on its principle, another undesired side effect results for the patient. For imaging, it is necessary that x-rays are absorbed. This also means, however, that a part of the x-ray radiation is be absorbed during therapy. In order to compensate for this, either the power of the x-ray source or the irradiation time must be increased.

A change in the course of treatment could be a solution to the problem. Thus, for example, the balloon could first be filled with air or a contrast agent. After positioning and checking the shape, this medium will be replaced by the actual filling medium for the irradiation. This exchange, however, poses the risk that the positional relationships will change again. With the conventional use of contrast agent, after this exchange has been made, it is difficult to say how complete this exchange was or whether there are any highly concentrated accumulations of contrast agent somewhere in the balloon catheter. The effect would be a non-uniform irradiation of the tumor bed, since residues of the contrast agent locally absorb the x-ray radiation in a limited manner. A complete killing of the tumor cells is therefore not assured.

In another context, a balloon catheter is known from WO 99/04856 A1, with which the intensity of radiation that is emitted from a radiation source and strikes the tissue to be treated can be adjusted. The known balloon catheter has a catheter shaft as well as a first, outer balloon and a second, inner balloon disposed inside the outer balloon. An intermediate space is created between the inner balloon and the outer balloon in order to keep constant the distance between the balloons, and thus the volume of the intermediate space will be maintained constant. A liquid introduced into the intermediate space has the task of absorbing radiation. However, with this known solution, the above-named problem still cannot be solved.

Another solution for a balloon catheter with two balloons lying one inside the other is described in US 2005/0080313 A1. The two balloons are joined together over large regions in this known solution. The two balloons are detached from one another only at specific sites, so that a gap is formed into which a medium can be injected. In this way, individual regions of tissue may be excluded from irradiation. Also, with this solution, it is still not possible to solve the above-named problems with respect to placement of the balloon catheter.

SUMMARY OF THE INVENTION

Proceeding from the named prior art, the object of the present invention is to further develop a balloon catheter of the type named initially in such a way that the balloon catheter can be securely controlled with respect to its shape and position in a patient in a simple but clear manner prior to irradiation. In addition, a correspondingly improved applicator with balloon catheter will be provided.

This object will be accomplished according to the invention by a balloon catheter, in particular for invasive radiotherapy, with a catheter shaft for introducing a probe, having a first, outer balloon and having a second, inner balloon, disposed inside the outer balloon, the inner space of the second, inner balloon connecting with a channel for connection to a media inlet, and intermediate space between the first, outer balloon and the second, inner balloon connecting to a channel for connection to a media storage unit, the balloon catheter characterized in that the outer balloon is formed of a flexible, non-extendible material and that the inner balloon is formed of a flexible, extendible material. This object will also be accomplished according to the invention by an applicator, in particular for invasive radiotherapy, having a balloon catheter, with a catheter shaft for introducing a probe, having a first, outer balloon made of a flexible, non-extendible material and a second, inner balloon made of a flexible, extendible material disposed inside outer balloon, additionally having an inside space of the second, inner balloon, which is connected via a connection channel at least temporarily with a media inlet, and additionally having an intermediate space between the first, outer balloon and the second, inner balloon, which is connected via a connection channel at least temporarily with a media storage unit. Further features and details of the invention can be taken from the subclaims, the description and the drawings. Features and details, which are described in connection with the balloon catheter according to the invention, of course, apply also in connection with the applicator according to the invention, and vice versa.

The balloon catheter according to the invention as well as the applicator according to the invention are particularly suitable for achieving visualization of balloon catheters in invasive radiotherapy. The present invention is based on a methodology and a device for enabling control of a balloon catheter with respect to its shape and position in a patient prior to an irradiation.

According to the first aspect of the invention, a balloon catheter, in particular for invasive radiotherapy, is provided, the catheter having a catheter shaft for introducing a probe, as well as a first, outer balloon and a second, inner balloon disposed inside the outer balloon, the inner space of the second, inner balloon being connected to a channel for connection to an inlet for media and the intermediate space between the first, outer balloon and the second, inner balloon being connected to a channel for connection to a media storage unit. The balloon catheter is therefore characterized according to the invention in that the outer balloon is formed of a flexible, non-extendible material and that the inner balloon is formed of a flexible, extendible material.

The balloon catheter according to the invention first of all has a catheter shaft for introducing a probe. In this way, the introduction of a probe, e.g., a radiation therapy probe is made possible.

In addition, the balloon catheter next provides a first, outer balloon (outer balloon). This outer balloon according to the invention is formed of a flexible, non-extendible material, the invention not being limited to specific materials. The outer balloon has a specific radius R1 and may be made of polyethylene PET, for example, or similar material.

In addition, the balloon catheter has a second, inner balloon (inner balloon) disposed inside the outer balloon. This inner balloon according to the invention is formed of a flexible, extendible material, the invention not being limited to specific materials. It is most of all important that the inner balloon is extendible. For example, the inner balloon can be made of a flexible, extendible material such as silicone, latex urethane, or similar material. The inner balloon in the standard state has a radius R2, which is smaller than the radius R1 of the outer balloon in the standard state. The standard state of the inner balloon is defined by the filling volume $V2=4/3 \times R2^3 \times Pi$, whereas the standard state of the outer balloon is defined by the filling volume $V1=4/3 \times R1^3 \times Pi$.

The balloon volume V2 of the inner balloon can be increased by further introduction of filling medium, since the inner balloon is made of extendible material. If, however, the volume V1 ($V1=4/3 \times R1^3 \times Pi$) of the outer balloon is reached, the inner balloon cannot be further expanded by further addition of filling medium. This is prevented by the non-extendible outer balloon. Further filling of the inner balloon in fact increases the pressure inside the balloon and thus improves the dimensional stability of the balloon, but without the danger of a balloon rupture. The dimensional stability offers a great advantage in comparison to balloon catheters made of flexible, extendible materials, since the particular features do not change during the irradiation. The balloon cannot be deformed by external influences and the optimal irradiation of the tumor bed is thus assured.

According to the invention, the inner space of the inner, second balloon is connected to a channel for connection to a media inlet. The inner balloon can thus be filled with a medium via the channel. In this way, the invention is basically not limited to specific types of media. Several advantageous, but non-exclusive examples will be explained in more detail in the further course of the description.

Finally, according to the invention, the intermediate space between the first, outer balloon and the second, inner balloon is connected to a channel for connection to a media storage unit. The intermediate space is thus bounded by the outer surface of the inner balloon and the inner surface of the outer balloon. The region between the two balloons is thus connected to the medium storage unit via the connection channel. A specific medium, by means of which the position of the balloon catheter can be examined precisely, can be found in the intermediate space, at least temporarily. The particulars of how this happens will be described in greater detail in the further course of the description, particularly in connection with the applicator according to the invention, so that reference is made here to the corresponding statements.

Advantageously, the outer balloon and the inner balloon are provided in the region of the distal end of the catheter shaft. Of course, the balloons could also be provided or disposed at other places on the catheter shaft.

The outer balloon and/or the inner balloon is/are preferably designed as spherical, cigar-shaped or elliptical, the invention not being limited to specific contours. A spherical configuration is viewed as particularly preferred.

In another configuration, a positioning device for positioning a probe can be advantageously provided in the catheter shaft in the region of the center of the inner balloon and/or of the outer balloon. For example, this may involve a limiting piece, for example, a mechanical limiting piece. A probe can then be introduced into the catheter shaft up to this positioning device and can be precisely positioned via the positioning device. It can be achieved thereby that the probe emits radiation in the desired amount and direction to the correct place. The positioning device is preferably found in the central point of the outer balloon and/or inner balloon.

According to another aspect of the invention, an applicator is provided, in particular for invasive radiotherapy, with a balloon catheter, having a catheter shaft for introducing a probe, having a first, outer balloon made of a flexible, non-extendible material and a second, inner balloon made of a flexible, extendible material disposed inside the outer balloon, additionally having an inner space of the second, inner balloon, which is connected via a connection channel to a media inlet, at least temporarily, and additionally having an intermediate space between the first, outer balloon and the second, inner balloon, which is connected via a connection channel to a media storage unit, at least temporarily.

Such an applicator is thus composed of the basic components: balloon catheter, media inlet and media storage unit.

It is advantageously provided that the intermediate space between the first, outer balloon and the second, inner balloon, the connection channel and the media storage unit are designed as a closed system. This means that medium is not introduced to the system from the outside, nor is medium withdrawn from this system.

Preferably, a defined media volume is provided in the closed system.

Advantageously, the media storage unit can be designed as a closed, non-extendible container or as a container made of a flexible, extendible material. Of course, the invention is not limited to these two embodiments. The medium storage unit can be designed in different implementation versions. In the case of a gaseous medium, for example, the use of a closed, non-extendible container is meaningful, since gases can be very well compressed. Gas need not be released or introduced, for which reason risks to the patient due to erroneous operation are minimized. The medium storage unit can also be made of a flexible, extendible material, however, so that it can take up the volume displaced from the intermediate region between the balloons. Also, instead of a closed container, a system which takes up the displaced medium or introduces it again in a defined manner can be temporarily connected. In the simplest case, it is an injection syringe or similar device.

Thus, it can also be advantageously provided that the media storage unit and/or the media inlet is/are connected to the connection channel in a detachable manner.

Several advantageous, but non-exclusive examples of suitable media will be described below. For example, the medium found in the media storage unit can be a liquid or a gas, in particular air, a dispersion in water or a liquid or gaseous contrast agent. For example, the medium introduced via the media inlet can be a liquid or a gas, in particular air, an aqueous solution, a solution of contrast agent or a physiological saline solution.

It is advantageously provided that a probe is introduced into the catheter shaft, at least temporarily. The probe is found inside the catheter shaft particularly during the intended use of the applicator.

As was described above, the balloon catheter, which is applied in the applicator according to the invention, is designed in the way according to the invention as described further above, so that everything that is stated in connection with the balloon catheter also applies in connection with the applicator.

The invention, as it is described with respect to the balloon catheter as well as the applicator, in addition also contains the following methodology:

A balloon catheter, which is folded together at first, is placed in the tissue to be treated. At this point in time, no medium is found in the inner balloon, so that the balloon catheter assumes its minimal size. The balloon catheter is positioned in the tissue to be treated and a probe is introduced in a defined manner into the catheter shaft, which forms a channel. The balloon catheter, however, can also be directly positioned in the tissue to be treated.

Subsequently, the inner balloon is filled via the connection channel from the media inlet up to a standard state V2. Filling can be accomplished in different ways, for example, manually with an injection syringe, in an automated manner with a pump system, or in a similar way. The filling medium, which is found in the intermediate region between the inner balloon and the outer balloon, is thus displaced from the region V2 to the intermediate region, where it first maintains the distance between the outer balloon and the inner balloon.

In this state, the position and shape of the balloon catheter in the patient can be examined with different imaging methods and corrected if necessary. The prerequisite for this is the presence of a medium in the intermediate space between the balloons, which is sufficiently different from the surrounding tissue, so that it can be utilized for the imaging.

If the balloon catheter lies correctly, additional medium is introduced from the media inlet via the connection channel into the inner balloon until the inner balloon has expanded enough that it is applied closely to the outer balloon. In this way, the medium from the intermediate space between the balloons is displaced into the medium storage unit. In this state, the irradiation of the tumor bed can be performed.

The contrast medium for visualization is withdrawn from the irradiation field without reduction in pressure in this method. Because the pressure is maintained, the advantage results that the positional relationships between probe, balloon catheter, and tissue to be treated do not change. For this reason, it is advantageous to provide the intermediate space between the balloons, the connection channel, and the medium storage unit as a closed system. Another advantage results due to the only temporary presence of a contrast agent in the irradiation field. In this way, there is no unintended absorption of radiation during the actual irradiation, for which reason the dose can be decreased or the irradiation time can be minimized.

After the irradiation, the inner balloon can be completely emptied via the connection channel, so that the total diameter of the balloon catheter is also minimized. The balloon catheter can be removed again after the probe is removed.

In the case of a fractionated irradiation, the balloon catheter usually remains in the patient and another irradiation is performed at a later time point. The positional relationships of probe, balloon catheter, and tissue to be treated are repeatedly examined prior to each irradiation. For this, the above-described procedure can be reversed as follows. The filling medium is allowed to partly leave the inner balloon via the connection channel, until the inner balloon has reached its standard state V2. In this way, medium flows from the media storage unit into the intermediate space between the balloons due to the changing pressure ratios. The medium, however, can also be actively introduced repeatedly. The positional relationships now can be examined again with imaging methods and can be corrected as needed. Subsequently, as has already been described, the treatment will continue.

BRIEF DESCRIPTION OF THE DRAWINGS

The invention will now be explained in more detail on the basis of embodiment examples with reference to the appended drawings. Here.

DETAILED DESCRIPTION OF THE INVENTION

An applicator 50 with a balloon catheter 10, which can be used for invasive radiotherapy, is shown in FIGS. 1 to 4.

Figure 1:
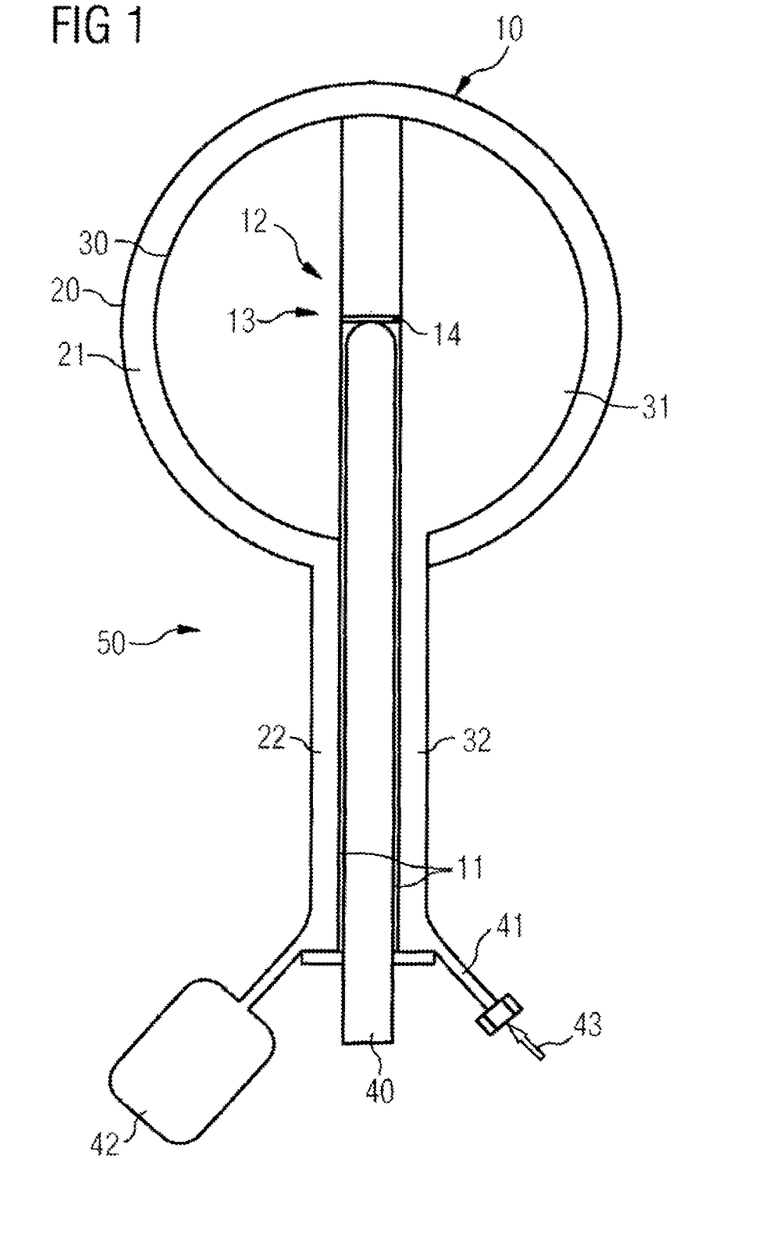
FIG. 1 shows the basic structure of an applicator according to the invention.

FIG. 1 first shows the basic structure of applicator 50. The latter provides a balloon catheter 10, comprising a catheter shaft 11. In the region of distal end 12 of catheter shaft 11, a positioning device 14 in the form of a limiting piece is provided in order to position a probe 40 introduced in catheter shaft 11.

In addition, an outer balloon 20 and an inner balloon 30 found inside outer balloon 20 are provided in the region of distal end 12 of catheter shaft 11. Inner balloon 30 bounds an inner space 31, which is connected via a connection channel 32 to a media inlet 41, by means of which a medium 43 is introduced, but which also can be drawn off again. An intermediate space 21, which is connected via a connection channel 22 to a medium storage unit 42, is bounded by the walls of inner balloon 30 and outer balloon 20.

As is additionally shown in FIG. 1, positioning device 14 is found in the region of the center 13 of the balloons, both inner balloon 30 and outer balloon 20.

The applicator 50 shown in FIGS. 1 to 4 shall serve for the purpose of irradiating a tumor bed.

The example of embodiment shown in the figures describes both a methodology as well as an apparatus in order to control balloon catheter 10 with respect to its shape and position in the patient prior to the irradiation.

Figure 3:
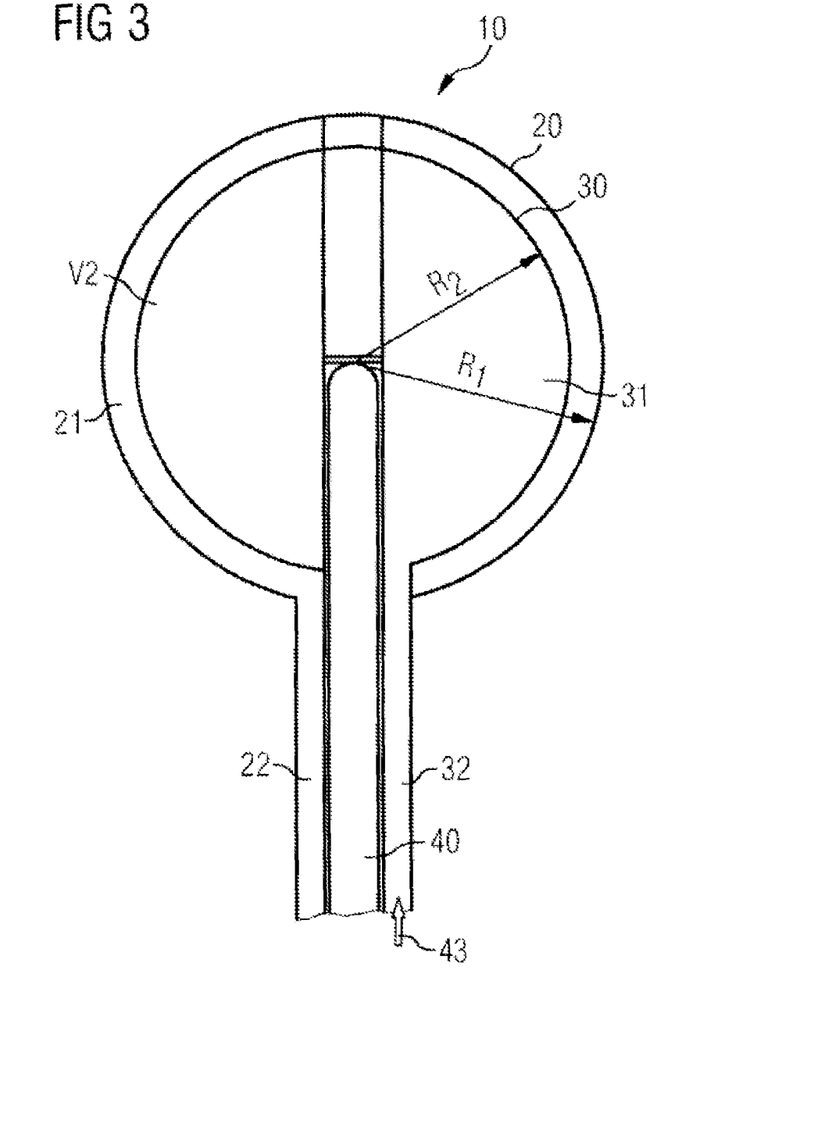
FIG. 3 shows the applicator in the state when its position is being examined.

FIG. 1 shows the schematic structure of a balloon catheter 10 in spherical shape. The shape of the balloon, however, may also be cigar-shaped, elliptical, or similar shape. Balloon catheter 10 comprises the outer balloon 20 and the, particularly smaller, inner balloon 30. The outer balloon with radius R1, as is shown in FIG. 3, comprises a flexible, non-extendible material such as polyethylene PET, for example. In contrast, inner balloon 30 can be made of a flexible, extendible material such as, for example, silicone, latex urethane, or similar material.

Inner balloon 30 in the standard state has the radius R2, as is shown in FIG. 3. The standard state is defined by the filling volume $V2=4/3\times R2^3\times Pi$.

Catheter shaft 11 makes possible the introduction of a probe 40 up to the region of the center 13 of balloons 20, 30. A mechanical limiting piece 14 aids the precise positioning of probe 40 in balloon center 13. This limiting piece 14 is not absolutely necessary.

Intermediate space 21 between the two balloons, outer balloon 20 and inner balloon 30, is thus connected to medium storage unit 42 via connection channel 22. A defined volume of a medium in the form of air, a dispersion in water or a liquid contrast agent is found in this closed system.

Inner balloon 30 can be filled with a medium 43 via connection channel 32. Medium 43 can be air, water, or a solution of contrast agent.

The balloon volume V2 of inner balloon 30 can be increased by further introduction of filling medium, since inner balloon 30 is made of extendible material. If, however, the volume V1 ($V1=4/3\times R1^3\times Pi$) of outer balloon 20 is reached, inner balloon 30 cannot be further expanded by further introduction of filling medium to inner balloon 30. This is prevented by the non-extendible outer balloon 20. Further filling of the inner balloon in fact increases the pressure in inner space 31 of inner balloon 30 and thus improves the dimensional stability of the inner balloon, but without the danger of a balloon rupture. The dimensional stability offers a great advantage in comparison to balloon catheters made of flexible, extendible materials, since the particular features do not change during the irradiation. The balloon cannot be deformed by external influences and the optimal irradiation of the tumor bed is thus assured.

Figure 2:
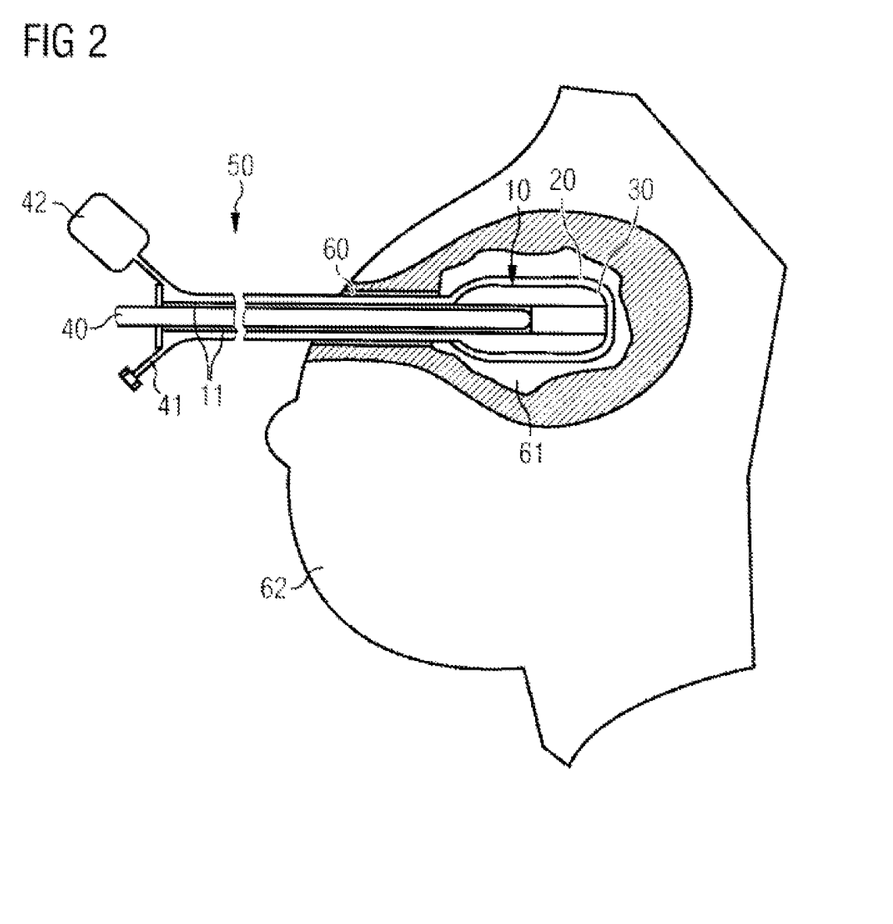
FIG. 2 shows the applicator when it is introduced into the tissue to be treated.

As is shown in FIG. 2, balloon catheter 10, which is first folded together, is placed in tumor bed 61 by means of a biopsy channel 60. At this point in time, no medium is found in inner balloon 30, so that balloon catheter 10 assumes its minimum size and can be introduced into biopsy channel 60. Balloon catheter 10 is positioned in tumor bed 61 and probe 40 is introduced into catheter shaft 11 in a defined manner. FIG. 2 shows the principle on the example of a breast 62. Balloon catheter 10, however, can also be placed in tumor bed 61 directly over the surgical access [for] tumor extraction.

Inner balloon 30 is subsequently filled via connection channel 32 to the standard state V2, which is shown in FIG. 3. Filling can be accomplished, for example, manually with an injection syringe, or in an automated manner with a pump system. The filling medium of intermediate space 21 between the two balloons 20, 30 is displaced from region V2 to the intermediate region where it is maintained and assures the distance between inner and outer balloons 20, 30.

In this state, the position and shape of balloon catheter 10 in the patient can be examined with different imaging methods and corrected if necessary. The prerequisite for this is the presence of a medium in the intermediate space 21 between the balloons, which is sufficiently different from the surrounding tissue, so that it can be utilized for the imaging. If balloon catheter 10 is placed correctly, additional medium 43 is added via connection channel 32 to inside space 31 of inner balloon 30, until inner balloon 30 has expanded enough that it is closely applied to outer balloon 20, as is shown in FIG. 4.

Figure 4:
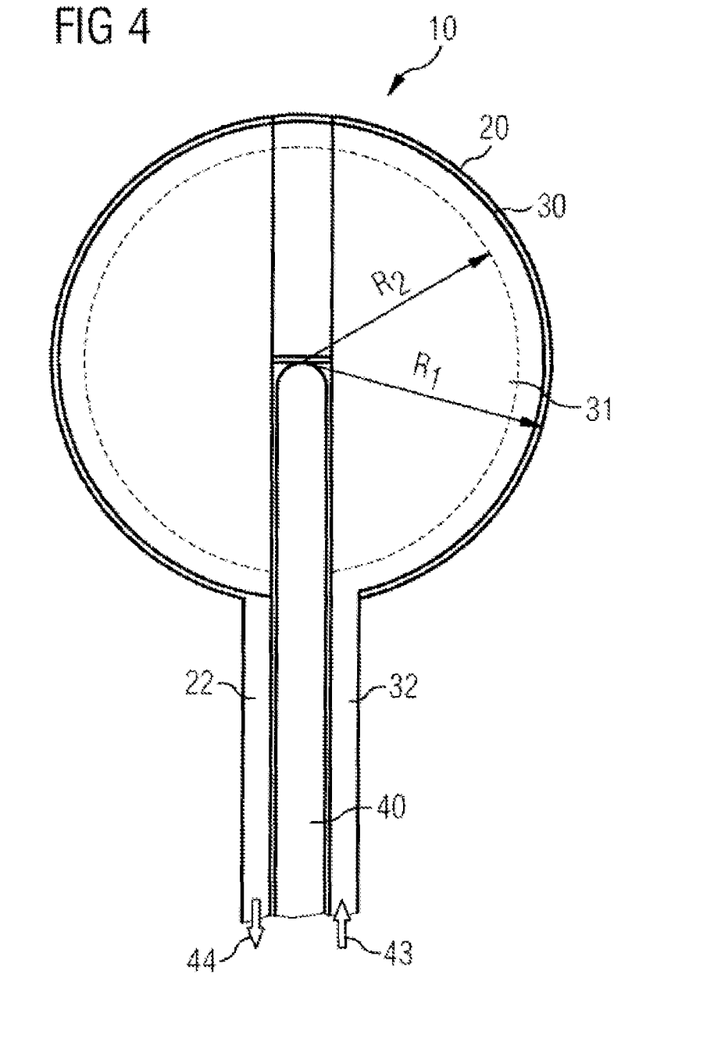
FIG. 4 shows the applicator in the state during an irradiation process.

The original size of inner balloon 30 is shown by the dotted line in FIG. 4. The medium is displaced thereby from intermediate space 21 between the balloons into medium storage unit 42, which is shown by arrow 44. In this state, the irradiation of tumor bed 61 can be performed. The contrast medium for visualization is withdrawn from the irradiation field without reduction in pressure in this method. Because the pressure is maintained, the advantage results that the positional relationships between probe 40, balloon catheter 10, and tumor bed 61 do not change. Another advantage results due to the only temporary presence of a contrast agent in the irradiation field. In this way, there is no unintended absorption of x-ray radiation during the actual irradiation, for which reason the dose can be decreased or the irradiation time can be minimized.

After the irradiation, inner balloon 30 can be completely emptied via connection channel 32, so that the total diameter of balloon catheter 10 is also minimized. After the removal of probe 40, balloon catheter 10 can be removed again through biopsy channel 60.

LIST OF REFERENCE NUMERALS

10 Balloon catheter
11 Catheter shaft
12 Distal end of the catheter shaft
13 Center of balloons
14 Positioning device (limiting piece)
20 Outer balloon (outer balloon)
21 Intermediate space
22 Connection channel
30 Inner balloon (inner balloon)
31 Inner space
32 Connection channel
40 Probe
41 Media inlet
42 Medium storage unit
43 Introduced medium
44 Direction for displacement of medium from the intermediate space
50 Applicator
60 Biopsy channel
61 Tumor bed
62 Breast
R1 Radius, standard state of outer balloon
R2 Radius, standard state of inner balloon
V2 Volume, standard state of inner balloon

What is claimed is:

1. A method of controlling a balloon catheter with respect to its shape and position in a tissue to be treated prior to an irradiation, the method comprising the steps of:
    placing a balloon catheter in a folded configuration in the tissue to be treated, wherein the balloon catheter is part of an applicator, said balloon catheter comprising a catheter shaft for introducing a probe, a first, outer balloon formed of a flexible, non-extendible material, a second, inner balloon, disposed inside the outer balloon, said inner balloon being formed of a flexible, extendible material, said inner balloon having an inner space, the inner space connecting with a channel for connection to a medium inlet, and an intermediate space between the outer balloon and the inner balloon, said intermediate space connecting via a channel for connection to a medium storage unit, whereby the intermediate space, the connection channel and the medium storage unit form a closed system wherein no medium is introduced to the closed system from outside the closed system and no medium is withdrawn from the closed system and whereby at least temporarily a defined medium volume, by which the position of the balloon catheter can be examined precisely, is disposed in the intermediate space;
    subsequently, filling the inner balloon via the connection channel from the medium inlet up to a standard state, wherein, in the standard state, the inner balloon has a filling volume V2, which is smaller than a filling volume V1 of the outer balloon and displacing medium, which is found in the intermediate space by the filling of the inner balloon to the standard state such that a distance between the outer balloon and the inner balloon is maintained in the standard state;
    examining the position and shape of the balloon catheter by use of imaging methods; and
    correcting the position and shape of the balloon catheter if necessary.

2. The method according to claim 1, wherein the medium, which is disposed in the intermediate space is a contrast medium.

3. A method of irradiating a tumor bed by use of a balloon catheter, the method comprising the steps of:
    controlling a balloon catheter with respect to its shape and position using a method according to claim 1, wherein the tissue to be treated is a tumor bed; and
    if the balloon catheter lies correctly, introducing more medium from the medium inlet via the connection channel into the inner balloon until the inner balloon has expanded enough that it is applied closely to the outer balloon, whereby medium from the intermediate space is displaced into the medium storage unit;
    subsequently, irradiating the tumor bed is irradiated.

4. The method according to claim 3, wherein the medium in the intermediate space is displaced into the medium storage unit without reduction in pressure.

5. The method according to claim 3, wherein at least temporarily a contrast medium is disposed in the intermediate space.

* * * * *